(12) United States Patent
Baskaran et al.

(10) Patent No.: US 12,397,090 B2
(45) Date of Patent: Aug. 26, 2025

(54) DEVICES AND METHODS FOR NITROSYLATION OF BLOOD

(71) Applicant: CASE WESTERN RESERVE UNIVERSITY, Cleveland, OH (US)

(72) Inventors: Harihara Baskaran, Beachwood, OH (US); Jonathan S. Stamler, Shaker Heights, OH (US); James D. Reynolds, Cleveland, OH (US); Jim A. Berilla, Highland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1621 days.

(21) Appl. No.: 16/619,228

(22) PCT Filed: Jun. 7, 2018

(86) PCT No.: PCT/US2018/036413
§ 371 (c)(1),
(2) Date: Dec. 4, 2019

(87) PCT Pub. No.: WO2018/226929
PCT Pub. Date: Dec. 13, 2018

(65) Prior Publication Data
US 2020/0164122 A1 May 28, 2020

Related U.S. Application Data

(60) Provisional application No. 62/516,985, filed on Jun. 8, 2017.

(51) Int. Cl.
*A61M 1/02* (2006.01)

(52) U.S. Cl.
CPC ... *A61M 1/0281* (2013.01); *A61M 2202/0275* (2013.01); *A61M 2206/10* (2013.01); *A61M 2207/00* (2013.01)

(58) Field of Classification Search
CPC ............ A61M 1/02; A61M 1/16; A61M 1/36; A61M 1/69; A61M 1/0281;
(Continued)

(56) References Cited

U.S. PATENT DOCUMENTS 5,205,820 A 4/1993 Kriesel
2007/0196428 A1* 8/2007 Glauser .................. A61L 31/08
514/184

(Continued)

FOREIGN PATENT DOCUMENTS

CN 101084054 A 12/2007
CN 102397597 A 4/2012
(Continued)

OTHER PUBLICATIONS

CN 102397597 A—Translation (Year: 2012).*
(Continued)

*Primary Examiner* — Bobby Ramdhanie
*Assistant Examiner* — Boi-Lien Thi Nguyen
(74) *Attorney, Agent, or Firm* — Tarolli, Sundheim, Covell & Tummino LLP

(57) ABSTRACT

Devices and methods are provided herein for exchange between a first agent and a second agent. The device includes a first chamber having a first inlet and a first outlet with a first flow passageway extending between the first inlet and the first outlet for flowing a first agent through the first chamber. The device also includes a second chamber having a second inlet and a second outlet with a second flow passageway extending between the second inlet and the second outlet for flowing a second agent through the second chamber and a membrane positioned between the first flow passageway and the second flow passageway to allow exchange through the membrane of the first agent with the (Continued)

second agent. Methods of nitrosylating blood and methods of manufacturing the device are also provided.

12 Claims, 8 Drawing Sheets

(58) Field of Classification Search
CPC ...... A61M 2202/0275; A61M 2206/10; A61M 2207/00; A61M 1/1621; A61M 1/0272; A61M 1/1698; A61M 1/0259; A61K 33/00
See application file for complete search history.

(56) References Cited

U.S. PATENT DOCUMENTS

| | | | |
|---|---|---|---|
| 2010/0125235 A1 | 5/2010 | Cauley et al. | |
| 2011/0226686 A1 | 9/2011 | Maurer | |
| 2012/0070878 A1 | 3/2012 | Fink et al. | |

FOREIGN PATENT DOCUMENTS

| | | | | |
|---|---|---|---|---|
| CN | 103180032 A | 6/2013 | | |
| CN | 103283070 A | 9/2013 | | |
| FR | 2431315 A1 | 2/1980 | | |
| GB | 2024653 A | 1/1980 | | |
| JP | 2013534461 A | 9/2013 | | |
| JP | 2015519143 A | 7/2015 | | |
| JP | 2016517395 A | 6/2016 | | |
| WO | 02076529 A1 | 10/2002 | | |
| WO | WO-2007009496 A1 * | 1/2007 | .............. | A61M 1/16 |
| WO | WO 2011/150216 A1 | 12/2011 | | |
| WO | 20130181322 A1 | 12/2013 | | |
| WO | WO-2014070620 A1 * | 5/2014 | .......... | A61M 1/3603 |
| WO | WO 2014/134503 A1 | 9/2014 | | |
| WO | 2017/053805 A1 | 3/2017 | | |

OTHER PUBLICATIONS

Japanese Office Action for corresponding Japanese Application Serial No. 2019-567597, mailed Jan. 17, 2023, pp. 1-7.
Office Action issued in connection with corresponding Chinese Patent Application No. 201880047661.6, Dated Nov. 10, 2022, pp. 1-8.
Shimazutsu, Kazufumi et al., "Inclusion of a Nitric Oxide Congener in the Insufflation Gas Repletes S-Nitrosohemoglobin and Stabilizes Physiologic Status During Prolonged Carbon Dioxide Pneumoperitoneum", Clinical and Translational Science Journal, 2009, vol. 2, Issue 6, 8 pages.
Andriot, M. et al., "Inorganic Polymers: Silicones in Industrial Applications", Nova Sciences, Jan. 2009, 106 pages.
Yurcisin, Basil M. et al., "Repletion of S-Nitrosohemoglobin Improves Organ Function and Physiologic Status in Swine Following Brain Death", National Institutes of Heath, Ann Surg. Author Manuscript, May 2014, 15 pages.
International Search Report and Written Opinion mailed Oct. 22, 2018 for PCT Application No. PCT/US2018/036413, 16 pages.
Chinese Office ACtion for corresponding Chinese Application Serial No. 201880047661.6, dated Mar. 22, 2023, pp. 1-8.
Chinese Office Action for corresponding Chinese Application Serial No. 201880047661.6, issued Apr. 19, 2022, pp. 1-18.
Japanese Office Action for corresponding Japanese Application Serial No. 2023-148362, with a mailing date of Jul. 2, 2024, 4 pages.

* cited by examiner

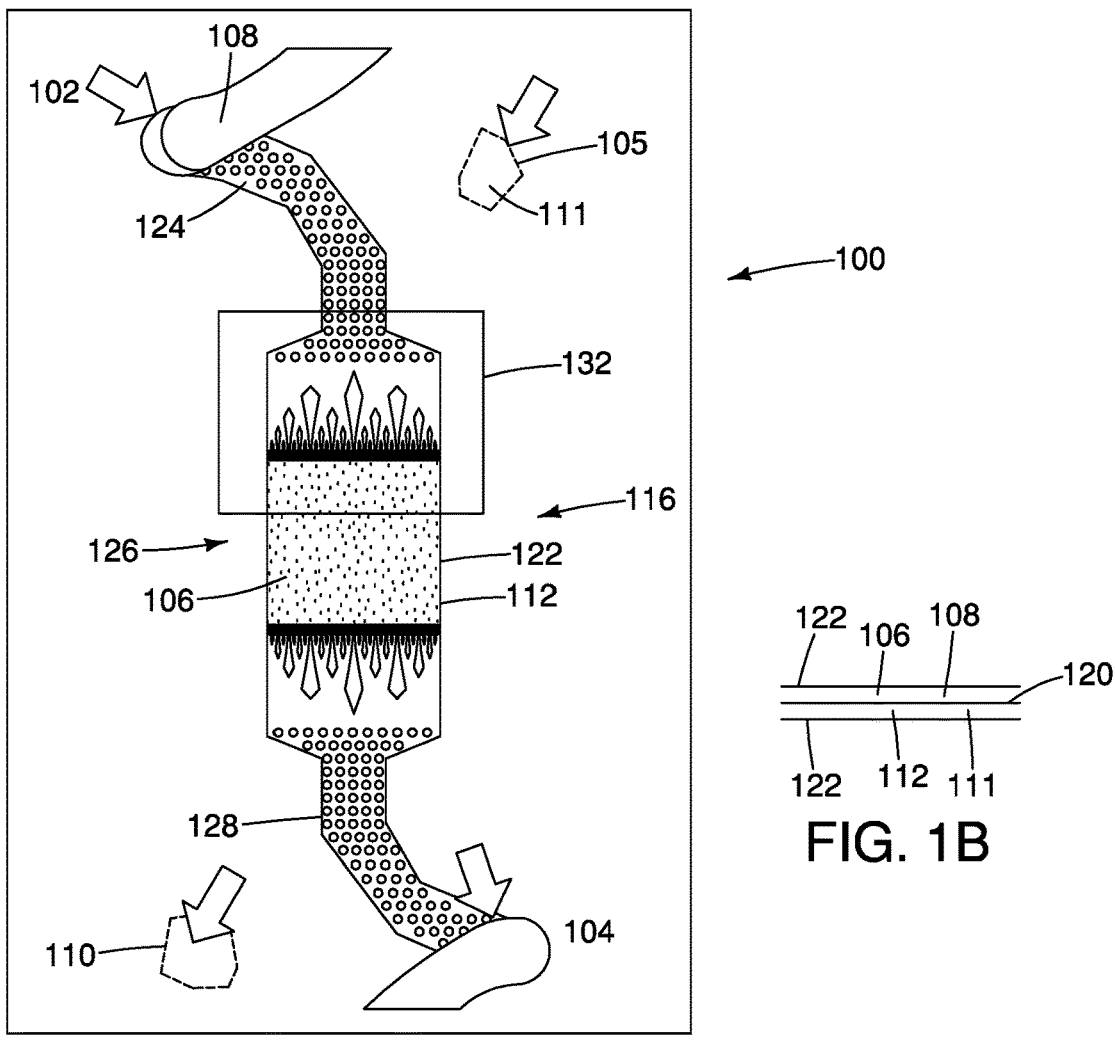
FIG. 1A
FIG. 1B
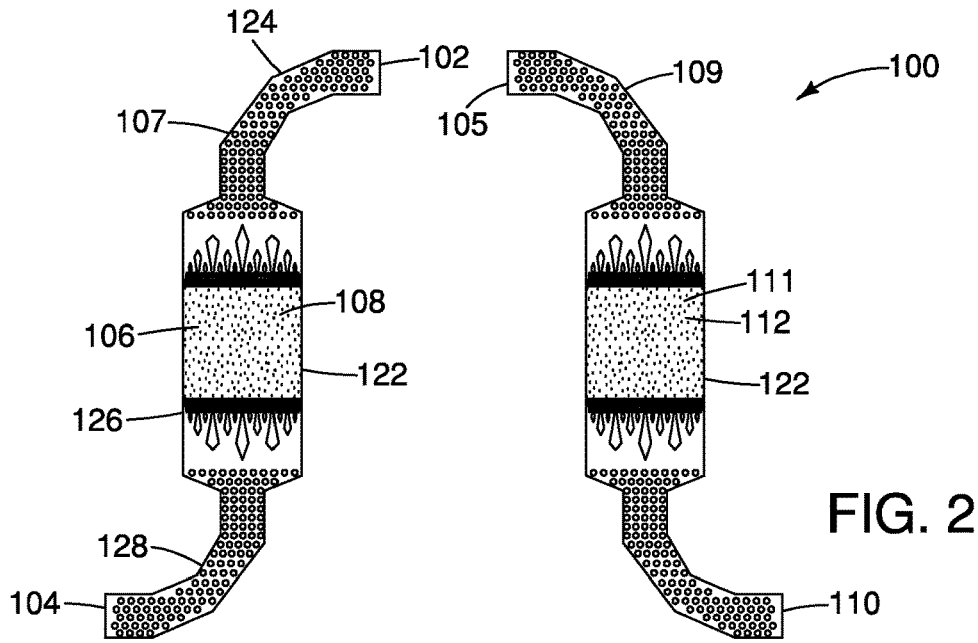
FIG. 2

DEVICES AND METHODS FOR NITROSYLATION OF BLOOD

CLAIM OF PRIORITY

This application is the national phase application of PCT/US2018/036413, filed on Jun. 7, 2018, which claims priority from U.S. Ser. No. 62/516,985 filed Jun. 8, 2017, both of which are is incorporated herein by reference in their entirety.

FEDERALLY SPONSORED RESEARCH OR DEVELOPMENT

This invention was made with government support under federal grant number N66001-13-C-4054 awarded by Defense Advanced Research Projects Agency, grant number 4UL1TR000439 awarded by the National Center for Advancing Translational Sciences (NCATS) at National Institutes of Health and grant number HL126900 awarded by the National Heart Lung and Blood Institute (NHLBI) at National Institutes of Health. The government has certain rights in the invention.

BACKGROUND

1. Technical Field

This application relates to nitrosylation of blood, and in particular to devices and methods for nitrosylation of blood for transfusion.

2. Background Information

It is desirable to nitrosylate blood prior to transfusion to restore nitric oxide (NO) bioactivity. Previously, pediatric oxygenators have been used to deliver ethyl nitrite (ENO) gas to attempt to restore NO bioactivity. However, nitrosylation is complicated by time-dependent variability during transfusion with SNO levels varying from almost zero to physiological range. In addition, variability in SNO levels has occurred during controlled flow rates, which can vary dramatically during transfusion.

Provided herein are a device for nitrosylating blood ex vivo with ENO, in gas or liquid form, and a method for using the device for the nitrosylation of blood ex vivo with ENO, in gas or liquid form. Methods of manufacturing the device are also provided.

BRIEF SUMMARY

Devices and methods are provided herein for exchange between a first agent and a second agent.

In one aspect, a device for exchange between a first agent and a second agent is provided. The device includes a first chamber having a first inlet and a first outlet with a first flow passageway extending between the first inlet and the first outlet for flowing a first agent through the first chamber. The device also includes a second chamber having a second inlet and a second outlet with a second flow passageway extending between the second inlet and the second outlet for flowing a second agent through the second chamber and a membrane positioned between the first flow passageway and the second flow passageway to allow exchange through the membrane of the first agent with the second agent.

In an embodiment, the first chamber and the second chamber each comprise a plurality of transport channels.

In an embodiment, the first chamber and the second chamber each comprises a first passageway and a second passageway.

In an embodiment, the first passageway and the second passageway each comprise structural members formed in the first and second passageways.

In an embodiment, the first chamber and the second chamber each comprise flow distribution members.

In an embodiment, the flow distribution members are positioned upstream from a plurality of transport channels in each of the first chamber and the second chamber.

In an embodiment, the device comprises a single module device.

In an embodiment, the device comprises a multiple module device comprising a plurality of first chambers and a plurality of second chambers.

In an embodiment, a wall of the first chamber or a wall of the second chamber forms the membrane for each module.

In an embodiment, the first chamber and the second chamber comprise poly(dimethyl siloxane) (PDMS).

In an embodiment, the membrane is permeable to a nitrosylating agent.

In an embodiment, the nitrosylating agent comprises ethyl nitrite.

In an embodiment, the device comprises a flow rate therethrough of about 10-1,200 µl/min. In an embodiment, the device comprises a flow rate therethrough of about 100 to about 1,100 µl/min, about 200 to about 1,000 µl/min, about 300 to about 900 µl/min, about 400 to about 800 µl/min, or about 500 to about 700 µl/min. In an embodiment, the device comprises a flow rate therethrough of about 1 to about 100 µl/min, about 100 to about 200 µl/min, about 200 to about 300 µl/min, about 300 to about 400 µl/min, about 400 to about 500 µl/min, about 500 to about 600 µl/min, about 600 to about 700 µl/min, about 700 to about 800 µl/min, about 800 to about 900 µl/min, about 900 to about 1,000 µl/min, about 1,000 to about 1,100 µl/min, or about 1,100 to about 1,200 µl/min.

In another aspect, a method of nitrosylating blood is provided. The method includes flowing blood through a first chamber of a device where the first chamber of the device is separated from a second chamber of the device by a membrane and flowing a nitrosylating agent through the second chamber of the device so that the blood is nitrosylated by the nitrosylating agent by exchange through the membrane.

In an embodiment, the nitrosylating agent is selected from the group consisting of ethyl nitrite, amyl nitrite, butyl nitrite, isobutyl nitrite, and tert-butyl nitrite. In an embodiment, the nitrosulating agent is ethyl nitrite. In an embodiment, the nitrosulating agent is amyl nitrite. In an embodiment, the nitrosulating agent is butyl nitrite. In an embodiment, the nitrosulating agent is isobutyl nitrite. In an embodiment, the nitrosulating agent is tert-butyl nitrite.

In an embodiment, the nitrosylating agent comprises ethyl nitrite (ENO).

In an embodiment, the method comprises flowing liquid ENO or ENO gas through the second chamber.

In an embodiment, the method comprises flowing the blood through the device at a flow rate of about 10-1,200 µl/min. In an embodiment, the device comprises a flow rate therethrough of about 100 to about 1,100 µl/min, about 200 to about 1,000 µl/min, about 300 to about 900 µl/min, about 400 to about 800 µl/min, or about 500 to about 700 µl/min. In an embodiment, the device comprises a flow rate therethrough of about 1 to about 100 µl/min, about 100 to about 200 µl/min, about 200 to about 300 µl/min, about 300 to about 400 µl/min, about 400 to about 500 µl/min, about 500 to about 600 µl/min, about 600 to about 700 µl/min, about 700 to about 800 µl/min, about 800 to about 900 µl/min, about 900 to about 1,000 µl/min, about 1,000 to about 1,100 µl/min, or about 1,100 to about 1,200 µl/min.

In an embodiment, the method comprises nitrosylating the blood to a final range of about 1-100 SNO/1000 Hb levels. In an embodiment, the method comprises nitrosylating the blood to a final range of about 10 to about 90 SNO/1000 Hb levels, about 20 to about 80 SNO/1000 Hb levels, 30 to about 70 SNO/1000 Hb levels, about 40 to about 60 SNO/1000 Hb levels, or about 50 SNO/1000 Hb levels. In an embodiment, the method comprises nitrosylating the blood to a final range of about 1 to about 90 SNO/1000 Hb levels, about 1 to about 80 SNO/1000 Hb levels, about 1 to about 70 SNO/1000 Hb levels, about 1 to about 60 SNO/1000 Hb levels, about 1 to about 50 SNO/1000 Hb levels, about 1 to about 40 SNO/1000 Hb levels, about 1 to about 30 SNO/1000 Hb levels, about 1 to about 20 SNO/1000 Hb levels, about 1 to about 10 SNO/1000 Hb levels.

In yet another aspect, a method of manufacturing a device for exchange between a first agent and a second agent is provided. The method includes providing a template, filling a cavity of the template with a polymer, and curing the polymer. The method also includes separating the cured polymer from the template to form a first chamber of a device and connecting the first chamber to a second chamber so that a membrane separates the first chamber from the second chamber.

In an embodiment, the polymer comprises poly(dimethyl siloxane) (PDMS).

In an embodiment, the method comprises providing a template having a plurality of structural members, a plurality of flow modification members and a plurality of transport chambers.

In an embodiment, the method comprises assembling the first chamber and the second chamber to form a single module device.

In an embodiment, the method comprises connecting tubing to an inlet and an outlet of the first chamber for flowing blood through the first chamber.

In an embodiment, the method comprises assembling a plurality of first chambers and second chambers together, each first chamber and second chamber having the membrane separating the first chamber from the second chamber.

In an embodiment, the method comprises providing a wall of the first chamber or the second chamber to form the membrane separating the first chamber from the second chamber.

BRIEF DESCRIPTION OF THE DRAWINGS

FIG. 1A illustrates an embodiment of a module of a device for nitrosylation.

FIG. 1B illustrates a partial sectional view of the device shown in FIG. 1A.

FIG. 2 illustrates an embodiment of two portions for forming the device shown in FIG. 1A showing alternating patterns for the portions.

DETAILED DESCRIPTION

Figure 3:
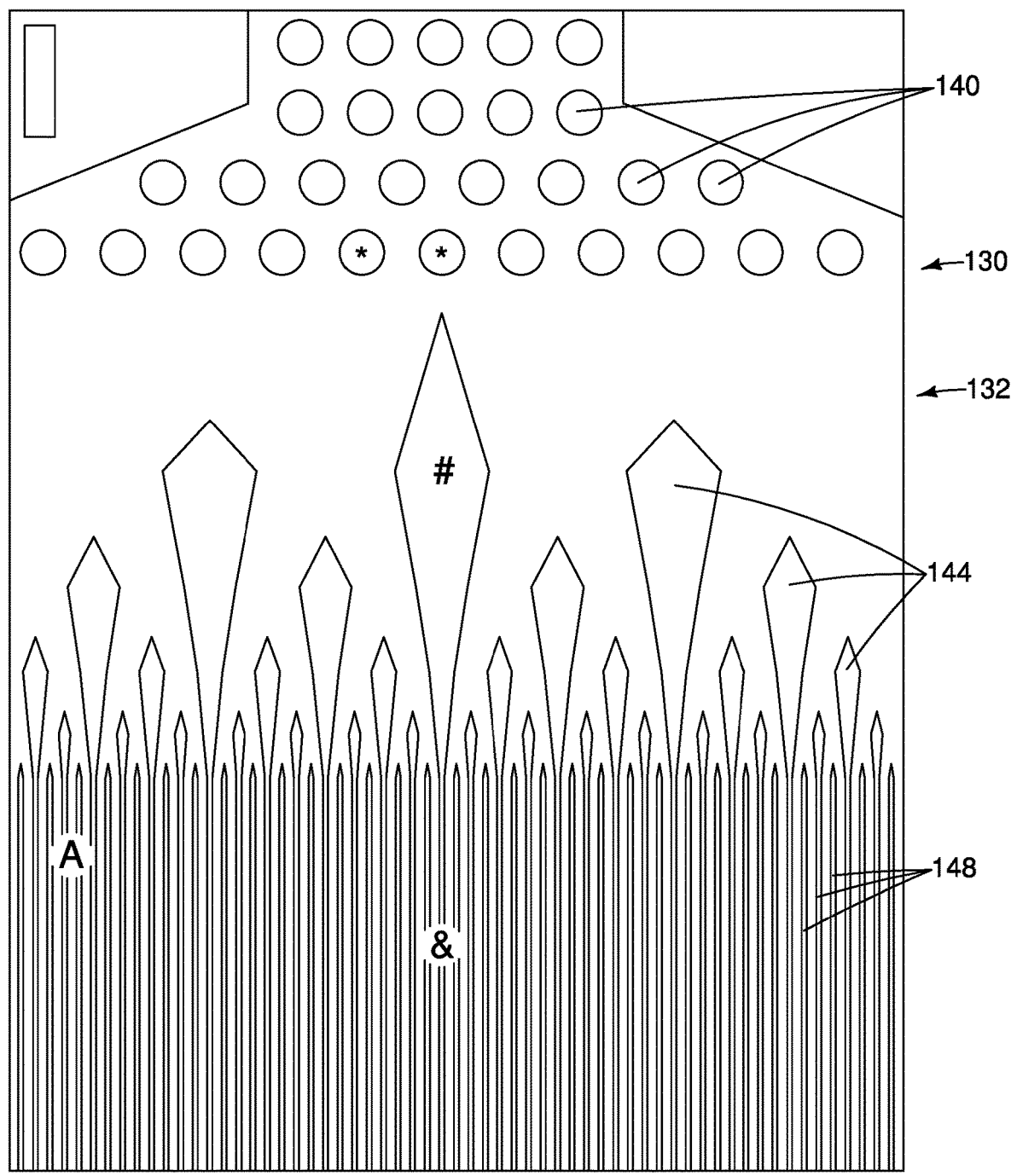
FIG. 3 illustrates partial view of an embodiment of a template for forming the portions of the device.

The embodiments disclosed below are not intended to be exhaustive or to limit the scope of the disclosure to the precise form in the following description. Rather, the embodiments are chosen and described as examples so that others skilled in the art may utilize its teachings.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the phrases "to cure the polymer," "curing the polymer" or "cured polymer" refers to the toughening or hardening of a polymer material by cross-linking of polymer chains, e.g., brought about by electron beams, ultraviolet radiation, heat, or chemical additives.

A device 100 for modifying blood ex vivo is shown in FIGS. 1A and 2. The device 100 includes a first inlet 102 and a first outlet 104 connected to a first chamber 106 having a first flow passageway 107 (shown in FIG. 2), for flowing a first agent 108 through the device 100. The first flow passageway 107 may extend from the first inlet 102 to the first outlet 104 through the device 100. In some embodiments, the first agent 108 may be blood. The device 100 may also include a second inlet 105 and a second outlet 110 connected to a second chamber 112 having a second flow passageway 109 for a second agent 111 in the device 100. The second flow passageway 109 may extend from the second inlet 105 to the second outlet 110 through the device 100. The second agent 111 may be in gas or liquid form. In some embodiments, the second agent may be a nitrosylating agent. By way of non-limiting example, the nitrosylating agent may be ethyl nitrite, amyl nitrite, butyl nitrite, isobutyl nitrite, tert-butyl nitrite and combinations thereof. In an embodiment, the nitrosulating agent is ethyl nitrite. In an embodiment, the nitrosulating agent is amyl nitrite. In an embodiment, the nitrosulating agent is butyl nitrite. In an embodiment, the nitrosulating agent is isobutyl nitrite. In an embodiment, the nitrosulating agent is tert-butyl nitrite. In an embodiment, the nitrosylating agent comprises ethyl nitrite (ENO). In some embodiments, the second agent 111 may be oxygen or any other agent 111 desirable to infuse into the first agent 108. The device 100 in FIG. 1A shows the first and second chambers 106, 112 assembled together. The first and second chambers 106, 112 mirror each other and form one module 116 of the device 100. When one single module 116 is used, a membrane 120 may be positioned between the first and second chamber 106, 112 as shown in FIG. 1B. The membrane 120 is permeable to allow exchange between the first agent 108 and the second agent 111. For example, the membrane 120 allows for nitrosylation of blood when blood is flowed through the first chamber 106 and a nitrosylating agent 111 is in the second chamber 112. The membrane 120 may be hydrophobic porous or non-porous polymer material. When multiple modules 116 are used together, a wall 122 of the first chamber 106 or the wall 122 of the second chamber 112 of one module 116 may form the membrane 120 of the adjacent module 116 having similar permeability as described in more detail below.

FIG. 2 illustrates the two portions of the device 100 that are mated together to form the module 116 shown in FIG. 1A. Two alternating patterns may be used to form the mirror images that join to form the chambers 106, 112 for the first agent 108 and the second agent 111. The alternating inlet 102 and outlet 104 allow for a single inlet 102 and a single outlet 104 even when multiple modules 116 are stacked together. In some embodiments, multiple inlets 102 and outlets 104 may be used. Similarly, a single second inlet 105 and a single second outlet 110 or multiple inlets 105 and outlets 110 may be used for the second chambers 112 when multiple modules 116 are assembled together. Tubing may be connected to the inlets and outlets for flowing the substances into and out of the modules 116. The chambers 106, 112 are described herein with reference to chamber 106. The chamber 112 is the mirror image of the chamber 106 and includes the same features as the chamber 106 described herein. As shown in FIGS. 1A and 2, the chamber 106 includes a first passageway 124 connected to the inlet 102. The first passageway 124 is connected to a central portion 126 that is connected to a second passageway 128 connected to the outlet 104.

FIG. 3 illustrates an example of a portion of a template 130 that may be used to form a pattern 132 in the walls 122 that form the chambers 106, 112 of the device 100 shown in FIG. 1A. FIG. 3 corresponds to the pattern 132 that is shown in the box in FIG. 1A. The walls 122 may be made from a polymer using the template 130 to mold the pattern 132 in the walls 122 of the device 100 to create the chambers 106, 112. As shown in FIG. 3, the template 130 includes several features for support and flow control of the first and/or second agents 108, 111 through the chambers 106, 112. The template 130 is used to form a plurality of support structures 140 (also indicated by *). As shown in FIGS. 1A and 2, the support structures 140 may be formed in the first passageway 124 and the second passageway 128. In some embodiments, the support structures 140 may extend into the central portion 126 of the chambers 106, 112. In some embodiments, the support structures 140 may be cylindrical, however, other shapes may also be used. By way of non-limiting example, support structures may be cylindrical, oval, triangular, polygonal, etc. The cylindrical structures 140 may be about 500 µm, for example for use with a 50 µm thick membrane 120 that separates the first agent 108 from the second agent 111. In some embodiments, the size range of the cylindrical structures may be about 100-1000 µm.

The template 130 may also be used to form flow distribution members 144 that may be positioned in the central portion 126 of the chambers 106, 112. As shown in FIG. 3, the flow distribution members 144 may be of different sizes and shapes. The flow distribution members 144 enable uniform distribution of flow in individual transport channels 148 in the chambers 106, 112. In some embodiments, the flow distribution members 144 may be tapered inward and/or outward to facilitate smooth flow through the chambers 106, 112. The flow distribution members 144 may be positioned on the upstream and/or downstream side of the individual transport channels 148. In some embodiments, the individual transport channels 148 may be about 100 µm (width)×100 µm (depth)×10 mm (length). In other embodiments, the transport channels 148 may be 50 µm (width)×50 µm (depth) and may be varied down to 10 µm. In some embodiments, the length of the individual transport channels may be about 10 mm to 100 mm. Each chamber 106, 112 may include $2^n$ channels 148, where n can range from 6 to 10. In some embodiments, the device 100 may include 32 or 64 transport channels 148. The size and number of the support structures 140, the flow distribution members 144 and the individual transport channels 148 will depend on the flow rate, the volume and the agents. In a single module 116 having 64 individual transport channels and dimensions 100 µm (width)×100 µm (depth)×10 mm (length), the area for interface between the first and the second agents is about 4.25 cm².

Figures 4A, 4B:
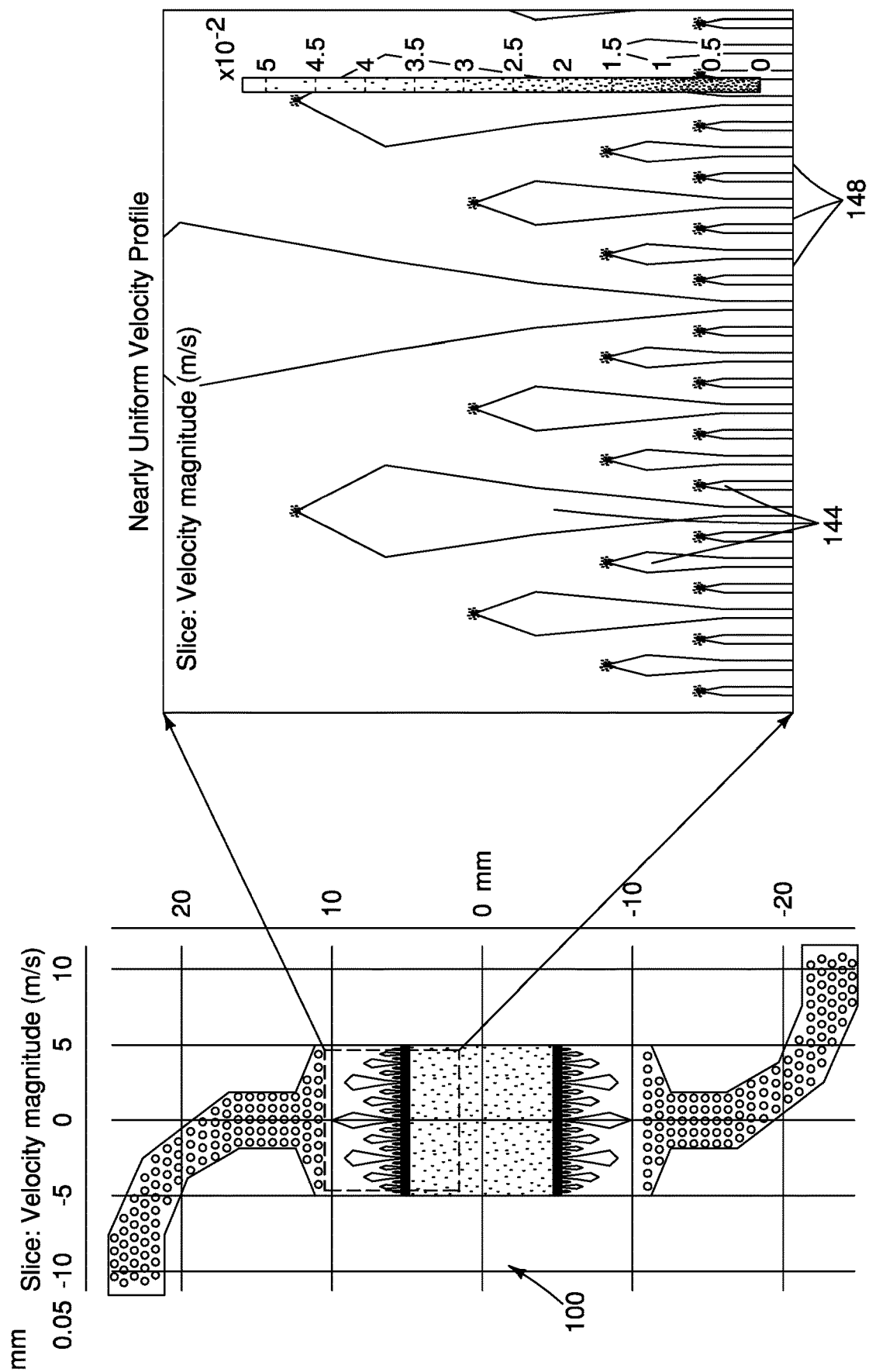
FIG. 4A illustrates a simulation showing uniform flow distribution in an embodiment the device.
FIG. 4B illustrates a simulation showing uniform flow distribution in the individual transport channels of an embodiment of the device.

FIG. 4A shows a simulation showing uniform flow distribution in the device 100 and FIG. 4B shows a simulation showing uniform flow distribution in the individual transport channels 148. The design of the chambers 106, 112 and the individual transport channels 148 allow for even flow and exchange between the agent 108 in the first chamber 106 and the second agent 111 in the second chamber 112 of the device 100 shown in FIG. 1.

Figure 5A:
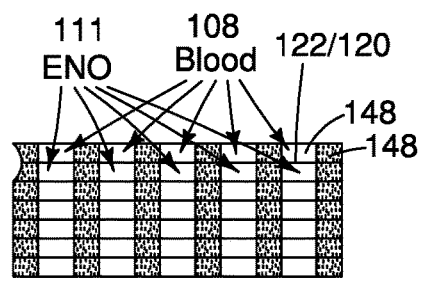
FIG. 5A illustrates a partial cross-sectional view of an embodiment of the device having multiple modules.
Figure 5B:
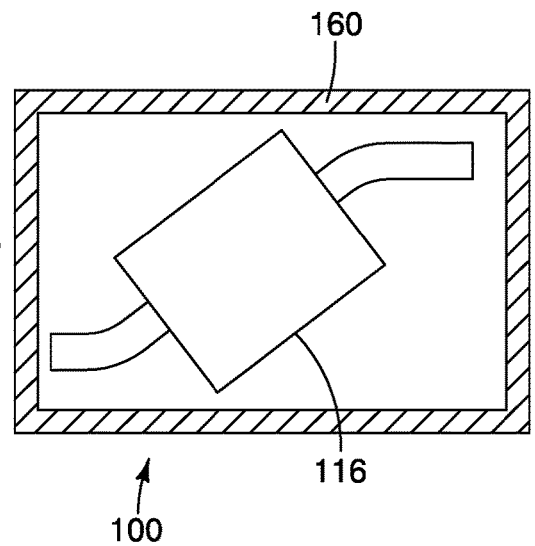
FIG. 5B illustrates a top view of an embodiment of a device having a frame.
Figure 6:
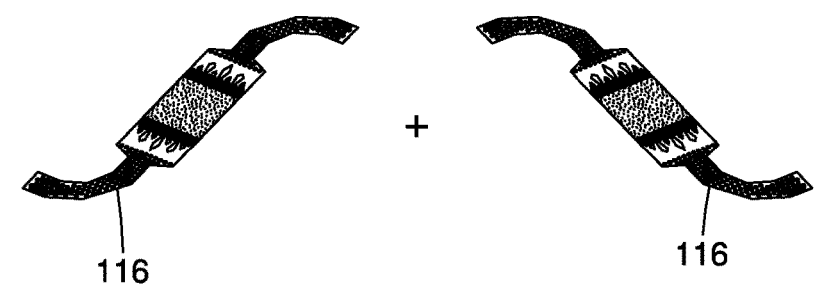
FIG. 6 illustrates an embodiment of a device that can be made including 50 modules assembled together.

FIGS. 5A, 5B and 6 illustrate the device 100 having a plurality of modules 116 assembled together. FIG. 5A is a cross-section through the individual transport channels 148 of the device 100 showing alternating first agent 108 and second agent 111 in the transport channels 148 with the wall 122 forming the membrane 120 between the first agent 108 and the second agent 111 where multiple modules 116 are stacked together. The wall 122 may be part of the first chamber 106 and/or the second chamber 112 when multiple modules 116 are stacked together so that the wall 122 forms the membrane 120. The wall 122 may be formed to be thin enough for exchange between the first agent 108 and the second agent 111. FIG. 5A illustrates seven alternating layers of transport channels 148 representing four modules 116. FIG. 6 illustrates an example showing that 50 modules 116 can be assembled together to form the device 100. Other numbers of modules 116 may be assembled together to form the device 100. The number of modules 116 assembled together may be any number and may be varied depending on the flow rate, the agents and the volume needed. In some embodiments, the device 100 having multiple modules 116 assembled together may include an outer frame 160 for additional support as shown in FIG. 5B. In some embodiments, the support frame 160 may be made from a metal, such as steel, including stainless steel.

In some embodiments, the overall thickness of each module 116 may be about 200 µm. A 1 mm thick device 100 includes about 5 modules 116 and a 1 cm thick device includes about 50 modules 116. In a 50 module device having 50 µm (width)×50 µm (depth) channels 148, the contact area for the first agent 108 and the second agent 111 through the membrane 120 is about $10^3$-$10^4$ cm²/cm³. By way of non-limiting example, when the first agent is blood and the second agent is a nitrosylating agent, the overall nitrosylation transport area in the device is about 1000 cm²/cm³. The volumes of the chambers 106 and 112 are about the same, in some embodiments the volume may be approximately 1.2 cm³. In some embodiments, the nitrosylation capability of the device 100 in blood is about 0.37 SNO/1000 Hb/10 cm²/50 ppm eNO driving force/125 µm polymer, using a 1 ml/min blood flow as a basis for the calculation. In some embodiments, the flow through each module 116 may range from about 10-1,200 µl/min and remain free from leaks of agents from the device 100. In an embodiment, the device comprises a flow rate therethrough of about 100 to about 1,100 µl/min, about 200 to about 1,000 µl/min, about 300 to about 900 µl/min, about 400 to about 800 µl/min, or about 500 to about 700 µl/min. In an embodiment, the device comprises a flow rate therethrough of about 1 to about 100 µl/min, about 100 to about 200 µl/min, about 200 to about 300 µl/min, about 300 to about 400 µl/min, about 400 to about 500 µl/min, about 500 to about 600 µl/min, about 600 to about 700 µl/min, about 700 to about 800 µl/min, about 800 to about 900 µl/min, about 900 to about 1,000 µl/min, about 1,000 to about 1,100 µl/min, or about 1,100 to about 1,200 µl/min.

The device 100 may nitrosylate blood to a stable physiological range of 1-5 SNO/1000 Hb levels and up to a range of 1-100 SNO/1000 Hb levels. In an embodiment, the method comprises nitrosylating the blood to a final range of about 10 to about 90 SNO/1000 Hb levels, about 20 to about 80 SNO/1000 Hb levels, 30 to about 70 SNO/1000 Hb levels, about 40 to about 60 SNO/1000 Hb levels, or about 50 SNO/1000 Hb levels. In an embodiment, the method comprises nitrosylating the blood to a final range of about 1 to about 90 SNO/1000 Hb levels, about 1 to about 80 SNO/1000 Hb levels, about 1 to about 70 SNO/1000 Hb levels, about 1 to about 60 SNO/1000 Hb levels, about 1 to about 50 SNO/1000 Hb levels, about 1 to about 40 SNO/1000 Hb levels, about 1 to about 30 SNO/1000 Hb levels, about 1 to about 20 SNO/1000 Hb levels, about 1 to about 10 SNO/1000 Hb levels.

The device 100 may be scaled for use in multiple transfusion conditions including: standard (1 unit of blood every 2-4 hours), rapid (1 unit of blood every hour), trauma (1 unit of blood every 10-15 minutes) or massive trauma (1 unit of blood every minute). In some embodiments, the flow rate may be about 500 ml/minute.

Figure 7:
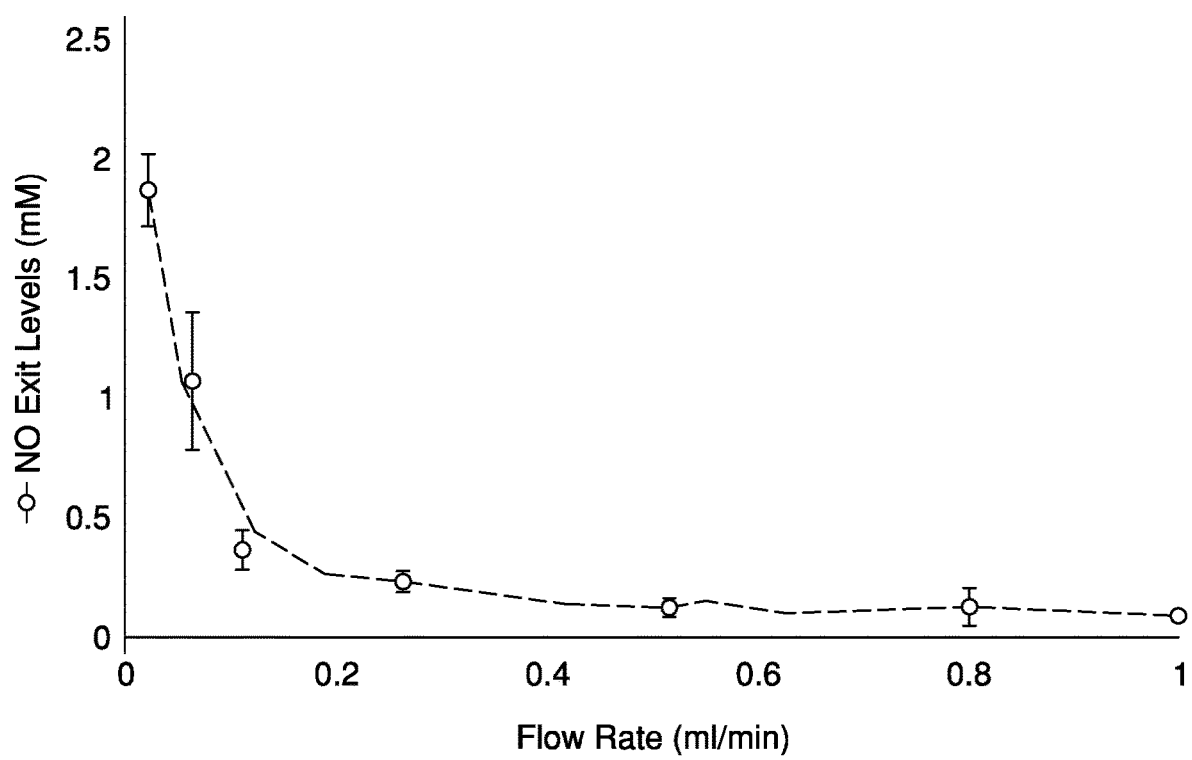
FIG. 7 illustrates an example showing NO exit levels versus flow rate.

FIG. 7 illustrates a graph showing control of nitrosylation of blood using the module 116 described above. The amount of NO in the blood exiting the device 100 may be modified by changing the flow rate through the device 100.

Figure 8A:
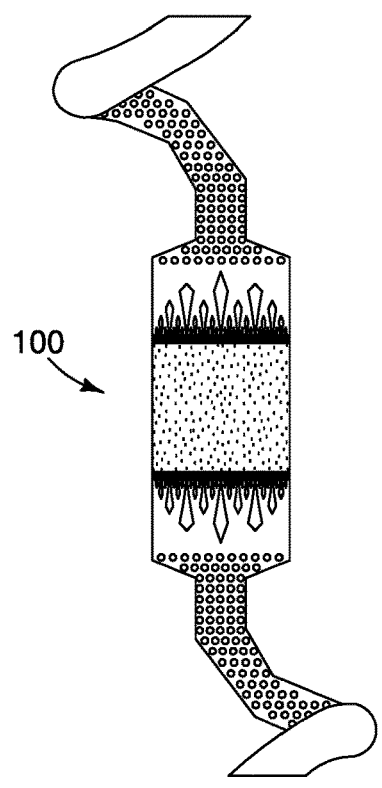
FIGS. 8A and 8B illustrate embodiments of devices having different amounts of nitrosylating agent being exchanged with blood. (8A: low, 8B: high).
Figure 8B:
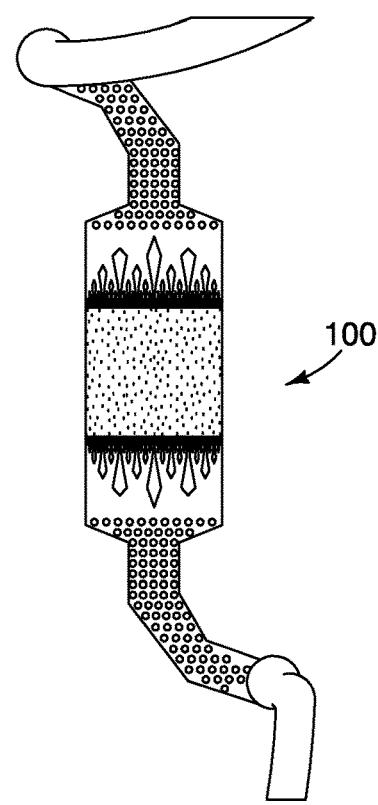

FIGS. 8A and 8B illustrate differences in the amount of the nitrosylating agent supplied to the device 100 in the second chamber 112 and exchanged with the blood in the first chamber 106. FIG. 8A shows a lower amount of nitrosylating agent being exchanged with blood flowing through the device 100 than FIG. 8B. FIG. 8B shows oxidation of the blood (demonstrated by the lighter color of blood flowing past the channels and out of the device). By way of non-limiting example, a device 100 having the membrane 120 with a thickness of about 50 µm between the first and second agents 108, 111 has a specific permeability value of about $8 \times 10^{-5}$ cm$^2$/min for the nitrosylating agent in a membrane 120 made from poly(dimethyl siloxane). The nitrosylation of the blood can be controlled using three design parameters of the device 100 including membrane thickness, overall flow rate of blood and nitrosylation agent levels. The device 100 is also compatible with oxygen transport.

Figure 9:
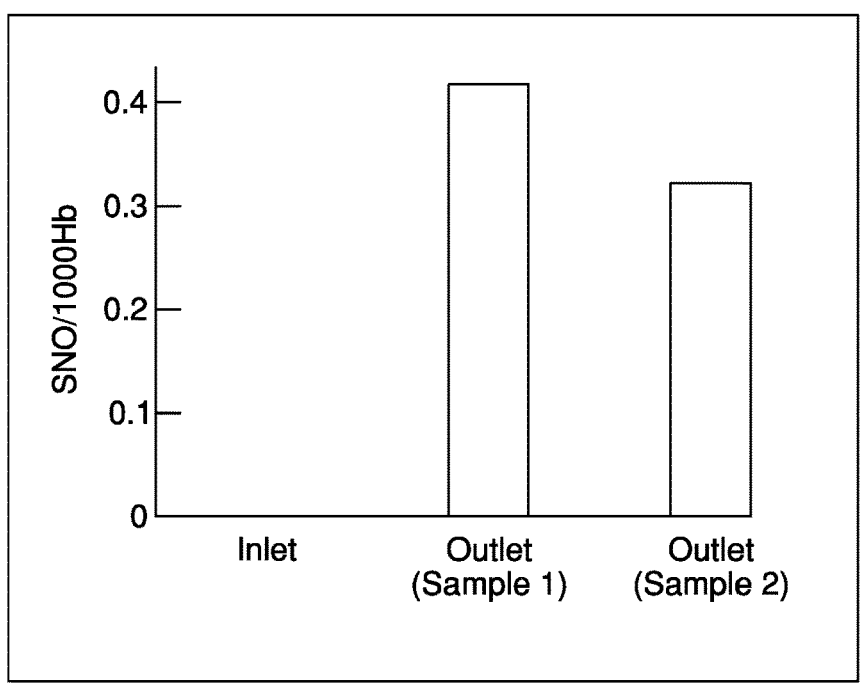
FIG. 9 illustrates an example of SNO/1000 Hb levels in two outlet samples versus an inlet sample.

FIG. 9 shows an example of renitrosylation of 7-day old blood samples using 50 ppm ENO as the second agent 111 in the second chamber 112 in a single module device 100 with a flow rate of 1 ml/min of blood in the first chamber 106 and a single pass through the device 100.

Methods for making the device 100 are also described herein. The modules 116 of the device may be made from different polymeric materials that can be used with the template 130 to form the pattern 132 for each chamber 106, 112 of the device 100. In some embodiments, different molecular weights of a polymer forming the chambers or membranes may be used to control nitrosylation rates. In some embodiments, poly(dimethyl siloxane) (PDMS) may be used to form the modules 116. Other polymers that may be used include UV curable vinyl ether polymers, poly (methyl methacrylate), but are not limited to these polymers.

In some embodiments, a carrier frame may be provided in which to build the modules described above. The frame may be made of stainless steel that is fabricated using photochemical milling. Each frame can hold multiple modules 116. In some embodiments, a frame may be milled to hold hundreds or thousands of modules. The frame may be sized and shaped to hold a plurality of templates for forming multiple chambers to make the modules. The templates may be registered within the frame using guide pins. In some embodiments, the templates may be manufactured using photolithography to produce one or more silicon wafer templates. Soft lithography may then be used to produce each layer/chamber of the device from the template.

Figure 10:
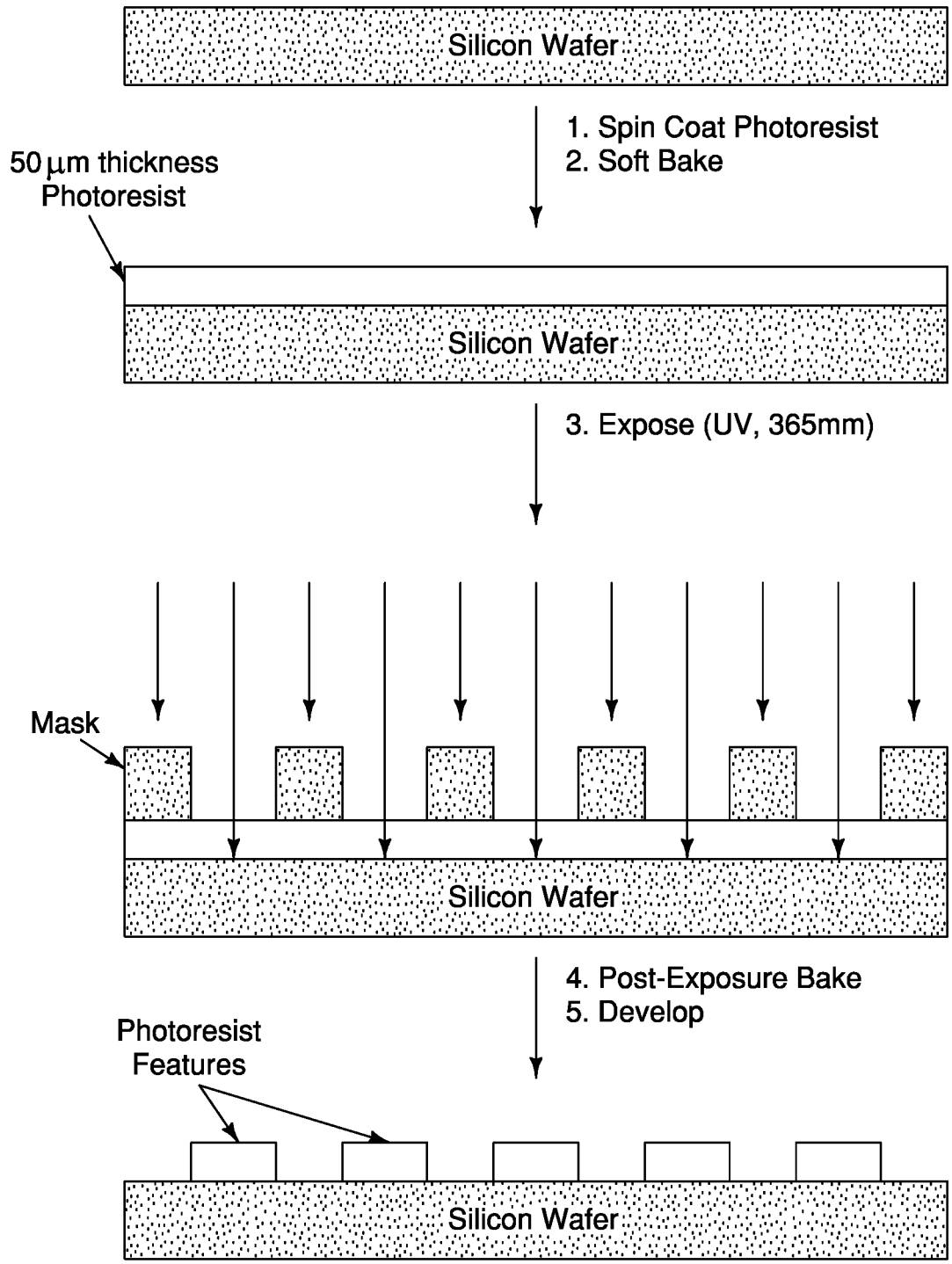
FIG. 10 illustrates an example of a photolithography process that may be used to form a template.

FIG. 10 illustrates an example of a photolithography process that may be used to form the template. Other processes known to one skilled in the art may also be used to form the template. As shown in FIG. 10, the template may be manufactured by covering a silicon wafer (e.g., University Wafer, Boston, MA) with photoresist (e.g., Su-850 photoresist, Micorchem, Newton, MA) by spin coating. The photoresist coated wafer is then soft baked. A mask is layered over the photoresist coated silicon wafer and the photoresist and mask are exposed to UV light. A post-UV exposure bake is performed and the wafer is developed (Su-8 developer, Microchem, Piranha Solution (3:1 H2SO4: H2O2 (30%)) with photoresist features that may be used for the template for forming the chambers of the device.

Figure 11:
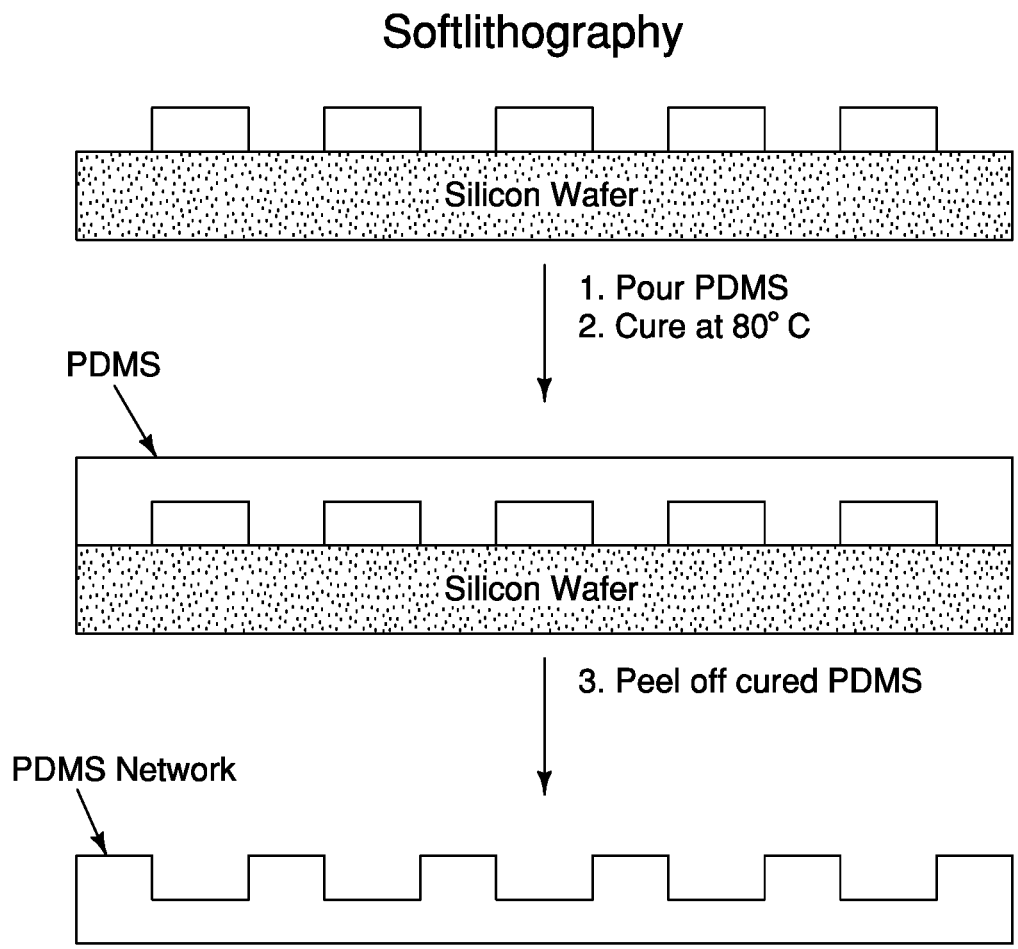
FIG. 11 illustrates an example of a soft lithography process that may be used with the template to form a chamber of the device.

FIG. 11 illustrates an example of a soft lithography process for forming a layer/chamber of the device using the template. Other processes known to one skilled in the art may also be used to form the chambers. Each cavity is filled with an uncured polymer, such as PDMS (e.g., Sylgard 184 base and curing agent, Dow Corning, MI). The template/polymer assembly is heated to cure the polymer. The cured polymer and template are separated (e.g., silanizing agent, tridecafluoro-1,1,2,2-tetrahydrooctyl trichlorosilane, United Chem, Horsham, PA) so that the cured polymer forms a layer/chamber of the device. In some embodiments, the template may be removed from the frame leaving the cured polymer in the frame. In some embodiments, the cured polymer may be removed from the frame. In a single module, a membrane may be added between the layers/chambers and connected using oxygen plasma bonding. The holes at the inlets and outlets may be punched out and tubing connected to the inlets and outlets. In a multimodular device, the alternating patterns may be layered on top of each other to form a plurality of modules assembled together, each module having a first and a second chamber or layer. The layers may be aligned and connected using oxygen plasma bonding. The holes at the inlets and outlets may be punched out and tubing connected to the inlets and outlets.

It is therefore intended that the foregoing detailed description be regarded as illustrative rather than limiting, and that it be understood that it is the following claims, including all equivalents, that are intended to define the spirit and scope of this invention.

The invention claimed is:

1. A device for exchange between a first agent and a second agent; the device comprising:
    a first chamber having a first inlet and a first outlet with a first flow passageway extending between the first inlet and the first outlet for flowing a first agent through the first chamber;
    a second chamber having a second inlet and a second outlet with a second flow passageway extending between the second inlet and the second outlet for flowing a second agent through the second chamber, wherein the second chamber is a mirror image of the first chamber; and
    a membrane formed by a portion of walls of the first chamber and a portion of walls of the second chamber where the portion of the walls of the first chamber contact the portion of the walls of the second chamber along a central portion of the first chamber and a central portion of the second chamber and positioned between the first flow passageway and the second flow passageway to enable exchange through the membrane of the first agent with the second agent,
    wherein the first chamber and the second chamber each comprise flow distribution members that extend along a flow direction of the first agent and the second agent, respectively, and wherein the flow distribution members of each of the first chamber and the second chamber are tapered to enable uniform distribution of flow of the first agent through the first chamber and the second agent through the second chamber.

2. The device according to claim 1, wherein the first chamber and the second chamber each comprise a plurality of transport channels, wherein the plurality of transport channels form a pattern in another portion of the walls of the first chamber and the second chamber, wherein the pattern of the plurality of transport channels comprise a plurality of bifurcations, wherein a number of the plurality of bifurcations increases towards the central portions of the first chamber and the second chamber.

3. The device according to claim 1, wherein the first chamber comprises a first passageway and a second passageway and the second chamber comprises another first passageway and another second passageway.

4. The device according to claim 3, wherein the first passageway and the second passageway each comprise structural members formed in the first and second passageways.

5. The device according to claim 1, wherein the flow distribution members are positioned upstream from a plurality of transport channels in each of the first chamber and the second chamber.

6. The device according to claim 1, comprising a single module device.

7. The device according to claim 1, comprising a multiple module device comprising a plurality of the first chambers and a plurality of the second chambers.

8. The device according to claim 7, wherein a wall of the first chamber or a wall of the second chamber forms the membrane for each module of the multiple module device.

9. The device according to claim 1, wherein the first chamber and the second chamber comprise poly(dimethyl siloxane) (PDMS).

10. The device according to claim 1, wherein the membrane is permeable to a nitrosylating agent.

11. The device according to claim 10, wherein the nitrosylating agent comprising ethyl nitrite.

12. The device according to claim 2, wherein the plurality of transport channels of each of the first chamber and the second chamber are formed side-by-side such that the first agent and the second agent are flowed in a same flow direction.

* * * * *